US012558059B2

(12) United States Patent
Tanaka

(10) Patent No.: US 12,558,059 B2
(45) Date of Patent: Feb. 24, 2026

(54) BODY CAVITY INSERTION-TYPE ULTRASOUND PROBE AND METHOD OF MANUFACTURING ACOUSTIC MATCHING LAYER

(71) Applicant: FUJIFILM Healthcare Corporation, Kashiwa (JP)

(72) Inventor: Hiroki Tanaka, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 21 days.

(21) Appl. No.: 18/624,314

(22) Filed: Apr. 2, 2024

(65) Prior Publication Data

US 2024/0341723 A1    Oct. 17, 2024

(30) Foreign Application Priority Data

Apr. 17, 2023    (JP) ................................. 2023-066850

(51) Int. Cl.
    *A61B 8/12*        (2006.01)
    *A61B 8/00*        (2006.01)
    *B06B 1/06*        (2006.01)
(52) U.S. Cl.
    CPC .............. *A61B 8/12* (2013.01); *A61B 8/4494* (2013.01); *B06B 1/0633* (2013.01); *B06B 1/067* (2013.01); *B06B 2201/76* (2013.01)

(58) Field of Classification Search
    CPC ......... A61B 8/0891; A61B 8/12; A61B 8/445; A61B 8/4483; A61B 8/4488; A61B 8/4494; B06B 1/0633; B06B 1/067; B06B 2201/76
    See application file for complete search history.

(56) References Cited

U.S. PATENT DOCUMENTS

2021/0169446 A1    6/2021    Weekemp et al.
2021/0177377 A1    6/2021    Song
2022/0087640 A1    3/2022    Minas et al.

FOREIGN PATENT DOCUMENTS

JP        2021-500981 A    1/2021
JP        2021-505263 A    2/2021
JP        2022-516078 A    2/2022

*Primary Examiner* — Michael T Rozanski
(74) *Attorney, Agent, or Firm* — Paul Teng

(57)            ABSTRACT

In a body cavity insertion-type ultrasound probe, acoustic matching between each transducer and a living body is improved. A film member (FPC substrate) is configured with a base film and a conductor layer. The conductor layer includes a signal pattern, a ground pattern, and a plurality of acoustic element arrays. An acoustic matching layer is provided between each transducer and the base film. The acoustic matching layer consists of an acoustic element array and a filling material. A ratio of a conductor material in the acoustic matching layer determines an acoustic impedance of the acoustic matching layer.

11 Claims, 11 Drawing Sheets

FIG.4

BODY CAVITY INSERTION-TYPE ULTRASOUND PROBE AND METHOD OF MANUFACTURING ACOUSTIC MATCHING LAYER

CROSS-REFERENCE TO RELATED APPLICATION

This application claims priority from Japanese Patent Application No. 2023-066850 filed on Apr. 17, 2023, the content of which is hereby incorporated by reference into this application.

BACKGROUND OF THE INVENTION

1. Field of the Invention

The present disclosure relates to a body cavity insertion-type ultrasound probe and a method of manufacturing an acoustic matching layer, and particularly relates to a structure of an acoustic matching layer.

2. Description of the Related Art

As a body cavity insertion-type ultrasound probe, an intravascular ultrasound (IVUS) probe, a bronchial ultrasound endoscope, or the like is known. The above-described probes are also called a catheter-type ultrasound probe, a small-diameter probe, or the like.

In an electronic scanning-type IVUS probe in the related art, a circular flexible printed circuit (FPC) substrate is disposed in a distal end portion thereof, and a transducer array having a circular-shaped form is provided inside the circular FPC substrate. Ultrasound waves emitted from the transducer array pass through the FPC substrate and are then emitted into a living body. An ultrasound beam is radially scanned by the transducer array.

The above-described FPC substrate is generally a film member including a base film and a conductor layer provided on a surface of the base film. The conductor layer has wiring patterns formed by a printing technique or the like. The conductor layer is configured with, for example, copper having a thickness of about 3 μm. In order to improve sensitivity or widen a band, it is desired to provide an acoustic matching layer between the FPC substrate and each transducer. However, since the IVUS probe is extremely thin (for example, about 1 mm in diameter), it is not easy to provide the acoustic matching layer between the FPC substrate and each transducer.

JP2021-500981A, JP2021-505263A, and JP2022-516078A disclose an electronic scanning-type IVUS probe. JP2021-500981A, JP2021-505263A, and JP2022-516078A do not disclose an acoustic matching layer including a part of a conductor layer in an FPC substrate.

SUMMARY OF THE INVENTION

An object of the present disclosure is to improve acoustic matching between a plurality of transducers and a living body. Alternatively, the object of the present disclosure is to make an acoustic matching layer by utilizing a part of a film member. The object of the present disclosure is to enable easy manufacture of an acoustic matching layer having a desired acoustic impedance.

According to an aspect of the present disclosure, there is provided a body cavity insertion-type ultrasound probe including: a film member including a base film and a conductor layer formed on the base film; and a plurality of transducers provided on the film member, in which a plurality of acoustic matching layers are provided between the base film and the plurality of transducers, the conductor layer includes a wiring pattern electrically connected to the plurality of transducers and a plurality of acoustic element arrays embedded in the plurality of acoustic matching layers, and a gap other than the acoustic element array in each of the acoustic matching layers is filled with a filling material.

According to an aspect of the present disclosure, there is provided a method of manufacturing an acoustic matching layer, the method including: a step of producing a film member by forming a conductor layer including an acoustic element array on a base film; and a step of filling a gap that is other than the acoustic element array and that is between the base film and the transducer with a filling material, in a case where the transducer is disposed on the film member, in which the acoustic element array and the filling material function as the acoustic matching layer, and an acoustic impedance of the acoustic matching layer is determined by a presence ratio of the acoustic element array in the acoustic matching layer.

According to the present disclosure, acoustic matching between the plurality of transducers and the living body can be improved. Alternatively, according to the present disclosure, the acoustic matching layer can be made by utilizing a part of the film member.

Alternatively, according to the present disclosure, it is possible to easily manufacture an acoustic matching layer having a desired acoustic impedance.

BRIEF DESCRIPTION OF THE DRAWINGS

FIG. 4 is a yz cross-sectional view of the laminated structure according to the first example.

DESCRIPTION OF THE PREFERRED EMBODIMENTS

Figure 1:
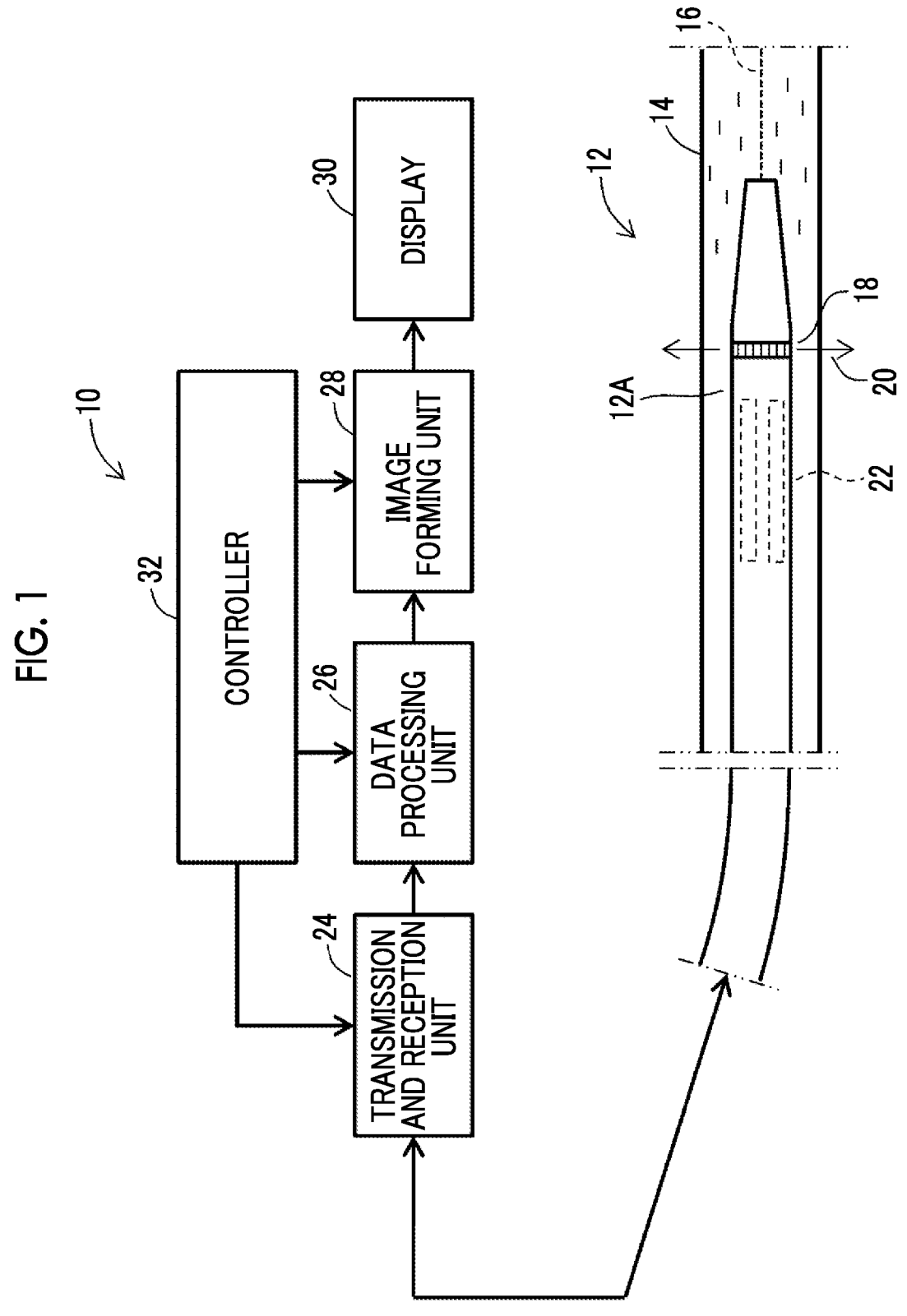
FIG. 1 is a diagram showing an ultrasound diagnostic apparatus according to an embodiment.

Hereinafter, an embodiment will be described with reference to the accompanying drawings.

(1) Outline of Embodiment

A body cavity insertion-type ultrasound probe according to an embodiment includes a film member having a base film and a conductor layer formed on the base film, and a plurality of transducers provided on the film member. A plurality of acoustic matching layers are provided between the base film and the plurality of transducers. The conductor layer includes wiring patterns that are electrically connected to the plurality of transducers and a plurality of acoustic element arrays that are embedded in the plurality of acoustic matching layers. A gap other than the acoustic element array in each acoustic matching layer is filled with a filling material.

According to the above-described configuration, a plurality of acoustic matching layers can be formed by using a part of the conductor layer provided in the film member. Therefore, it is possible to provide the acoustic matching layer for each transducer while avoiding an increase in a thickness of a laminate including the film member and the plurality of transducers. As a result, there is an advantage in improving sensitivity and expanding a frequency band. According to the embodiment, a plurality of acoustic element arrays can be easily formed by using a printing technique, a drawing technique, or the like.

In a case where a transducer arrangement direction is defined as a first direction and a direction orthogonal to the transducer arrangement direction is defined as a second direction, each acoustic element array is configured with a plurality of acoustic elements arranged in the first direction and the second direction, a plurality of acoustic elements arranged in the first direction, a plurality of acoustic elements arranged in the second direction, a plurality of acoustic elements having a random pattern that extends in the first direction and the second direction, and the like.

In the embodiment, an acoustic impedance of each acoustic matching layer is smaller than an acoustic impedance of each transducer and is larger than an acoustic impedance of a living body tissue. In the embodiment, the acoustic impedance of each acoustic matching layer is an acoustic impedance according to a presence ratio of a conductor material in each acoustic matching layer. Since it is easy to change a layout of the acoustic element array in each acoustic matching layer, a desired acoustic impedance can be easily obtained as the acoustic impedance of each acoustic matching layer.

In the embodiment, the wiring pattern includes a signal pattern and a ground pattern. A living body side end portion of each transducer includes a first portion and a second portion that are separated in a direction orthogonal to the transducer arrangement direction. The first portion in each transducer is connected to the signal pattern, and the second portion in each transducer is connected to the ground pattern. In each transducer, an acoustic element array is provided between the living body side end portion and the base film, and between the signal pattern and the ground pattern.

In the embodiment, a thickness of the signal pattern, a thickness of the ground pattern, and a thickness of each acoustic element array are the same. According to the above-described configuration, manufacturing costs can be reduced.

In the embodiment, the plurality of acoustic element arrays are electrically connected to the ground pattern included in the wiring pattern. According to the above-described configuration, it is possible to prevent an accumulation of electric charges in each acoustic element array.

In the embodiment, the thickness of each acoustic element array is the same as a thickness t of each acoustic matching layer. The thickness t satisfies a condition of $\lambda/10 \leq t < \lambda/2$ in a case where a wavelength corresponding to a center frequency of ultrasound waves emitted from each transducer is expressed by $\lambda$. According to the above-described configuration, it is possible for each acoustic matching layer to appropriately function. The center frequency of the ultrasound waves is generally a frequency corresponding to an intermediate point between two points that are a certain level below a peak in a frequency band of the ultrasound transducer.

In the embodiment, each transducer has the living body side end portion including two corner portions that extend in a direction orthogonal to the transducer arrangement direction. Each acoustic element array includes a plurality of acoustic elements that support two corner portions. According to the above-described configuration, an abnormal vibration mode is less likely to occur in the laminate, and an ultrasound wave propagation efficiency can be improved.

In the embodiment, a pitch included in the acoustic element array in each acoustic matching layer is smaller than a wavelength of a transverse wave generated by the filling material. According to the above-described configuration, it is difficult for transverse waves caused by the filling material to occur.

In the embodiment, the film member has a circular-shaped form, and the plurality of transducers are circularly aligned inside the film member. The ultrasound waves emitted from each transducer pass through the film member. The base film in the film member may function as an outer covering of the ultrasound probe.

A method of manufacturing an acoustic matching layer according to the embodiment includes a producing step and a filling step. In the producing step, the conductor layer including the acoustic element array is formed on the base film, and thus, the film member is produced. In the filling step, in a case where the transducer is disposed on the film member, the filling material fills a gap that is other than the acoustic element array and that is between the base film and the transducer. As a result, a portion consisting of the acoustic element array and the filling material functions as the acoustic matching layer. The acoustic impedance of the acoustic matching layer is determined by a presence ratio of the acoustic element array in the acoustic matching layer.

In the producing step, the conductor layer is formed by using a printing technique, a drawing technique, or the like. In the filling step, the filling material is introduced between the base film, in a spread state, and the transducer. The filling material is an adhesive material in the embodiment, the acoustic matching layer is produced by being filled with the filling material, and at the same time, the transducer is integrated with the base film. According to the above-described manufacturing method, the acoustic element array can be easily formed, that is, the acoustic matching layer can be easily formed.

In the embodiment, a plate-shaped piezoelectric material is placed on the film member, the filling material is introduced between the base film and the piezoelectric material, and the plurality of transducers are formed by dicing the piezoelectric material. In the above-described process, a disposition of the piezoelectric material on the film member corresponds to a disposition of the plurality of transducers on the film member.

(2) Details of Embodiment

FIG. 1 shows an ultrasound diagnostic apparatus according to the embodiment. The ultrasound diagnostic apparatus is used for ultrasound examination of a subject to be examined.

The ultrasound diagnostic apparatus includes an apparatus main body 10 and a body cavity insertion-type ultrasound probe (hereinafter, referred to as a probe) 12. Specifically, the probe 12 is an electronic scanning-type IVUS probe inserted into a blood vessel 14. The configuration described below may be applied to another probe (for example, a bronchial ultrasound endoscope).

The probe 12 is an elongated member having flexibility. A diameter of the probe 12 is, for example, within a range of 1 to 2 mm. The diameter of the probe 12 may be within or below the above-described range, or may be within or above the above-described range.

A distal end portion 12A of the probe 12 includes a transducer array 18 having a circular-shaped form. The transducer array 18 is configured with, for example, several tens or several hundreds of transducers arranged in a circular shape. An opening (transmission opening and reception opening) is set on the transducer array 18, and the ultrasound waves are emitted from the opening and the reflected waves are received by the opening. An ultrasound beam 20 is radially scanned by an electronic scanning of the opening.

An electronic circuit group 22 is provided in the distal end portion 12A. The electronic circuit group 22 is connected to the transducer array 18. The opening is scanned by an action of the electronic circuit group 22. The electronic circuit group 22 is configured with a plurality of electronic circuits. Each electronic circuit is configured with, for example, an application-specific integrated circuit (ASIC).

The probe 12 has a hollow passage formed along a central axis thereof. A guide wire 16 is inserted into the passage. More precisely, the probe 12 advances in a blood vessel along the guide wire 16 already disposed in the blood vessel 14.

A transmission and reception unit 24 is an electronic circuit that functions as a transmission beam former and a reception beam former. At a time of transmission, a plurality of transmission signals, output in parallel from the transmission and reception unit 24, are transmitted to the transducer array through the electronic circuit group 22. One transmission signal may be transmitted from the transmission and reception unit 24 to the electronic circuit group 22 on a premise that the electronic circuit group 22 performs beam forming for transmission. At a time of reception, a plurality of reception signals, output in parallel from the transducer array 18, are transmitted to the transmission and reception unit 24 through the electronic circuit group 22. The electronic circuit group 22 may perform sub-beam forming for reception. One reception signal may be transmitted from the electronic circuit group 22 to the transmission and reception unit 24 in one transmission and reception. In the transmission and reception unit 24, a phase addition is performed on the plurality of reception signals. As a result, reception beam data is generated. Along with a radial scanning, a plurality of pieces of reception beam data are sequentially transmitted from the transmission and reception unit 24 to an image forming unit 28 through a data processing unit 26.

The data processing unit 26 includes a wave detection circuit, a filter circuit, a logarithmic conversion circuit, and the like. The image forming unit 28 is configured with a digital scan converter (DSC). A tomographic image is formed from the plurality of pieces of reception beam data by the DSC. The tomographic image is displayed on a display 30. The tomographic image is a moving image or a still image showing a horizontal cross section of the blood vessel 14. The moving image or the still image showing a blood vessel longitudinal cross section may be displayed on the display 30. In this case, a tomographic image showing the blood vessel longitudinal cross section may be generated by connecting a plurality of pieces of horizontal cross-sectional data in a blood vessel central axis direction. A three-dimensional image may be displayed on the display 30.

A controller 32 includes a central processing unit (CPU) that executes a program. An operation of each component in the ultrasound diagnostic apparatus is controlled by the controller 32. A display is configured with an organic EL display device, a liquid-crystal display (LCD), or the like. An operation panel (not shown) is connected to the controller 32.

Figure 2:
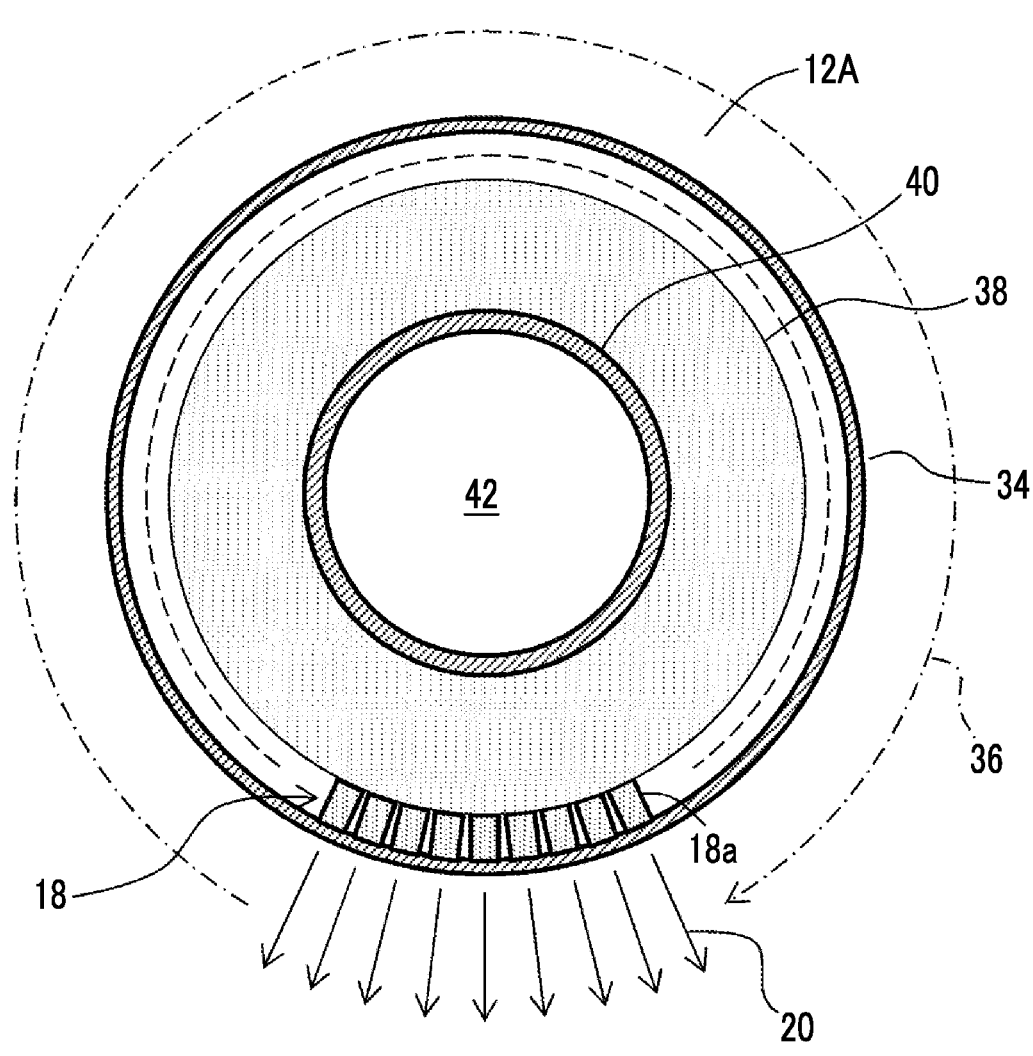
FIG. 2 is a horizontal cross-sectional view of a body cavity insertion-type ultrasound probe according to the embodiment.

FIG. 2 shows a cross section of the probe according to the embodiment. Specifically, in FIG. 2, a horizontal cross section of the distal end portion 12A is schematically shown. A film member 34 is an FPC substrate having flexibility in the embodiment. The film member 34 has a circular-shaped form. The transducer array 18 is provided inside the film member 34. The transducer array 18 is configured with a plurality of transducers 18a arranged in a circular shape. The ultrasound waves transmitted from each transducer 18a are transmitted through the film member 34 and are then emitted into a living body. A reflected wave from an inside of the living body is transmitted through the film member 34 and is then received by each transducer 18a. The ultrasound beam 20 is radially scanned as shown in FIG. 2 (refer to reference numeral 36).

A cylindrical-shaped backing 38 is provided inside the transducer array 18. The backing 38 is a member that attenuates the ultrasound waves emitted rearward from each transducer 18a. A pipe 40 is provided inside the backing 38. An inside of the pipe 40 is a passage 42 into which a guide wire is inserted.

Figure 3:
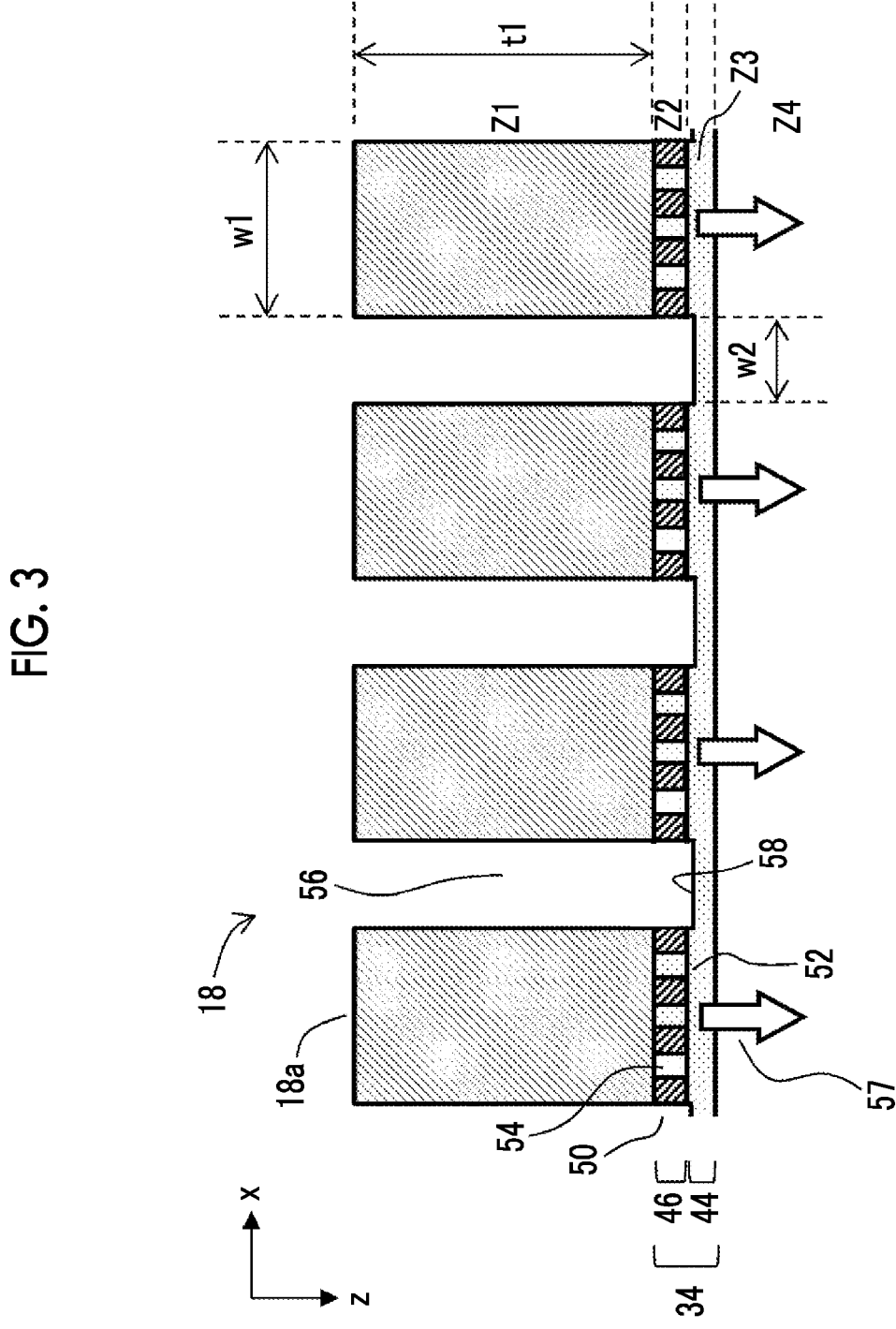
FIG. 3 is an xz cross-sectional view of a laminated structure according to a first example.
Figure 4:
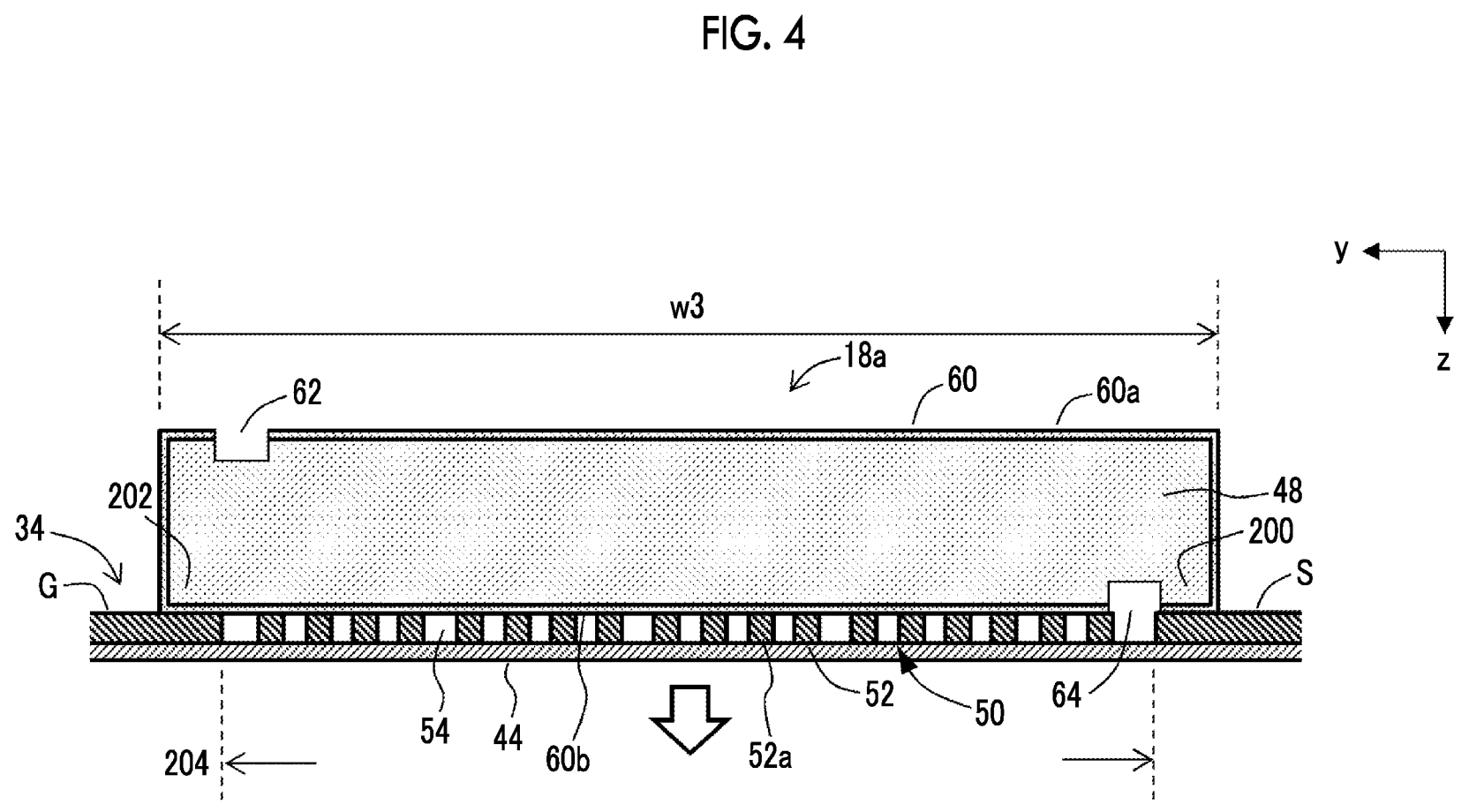
Figure 5:
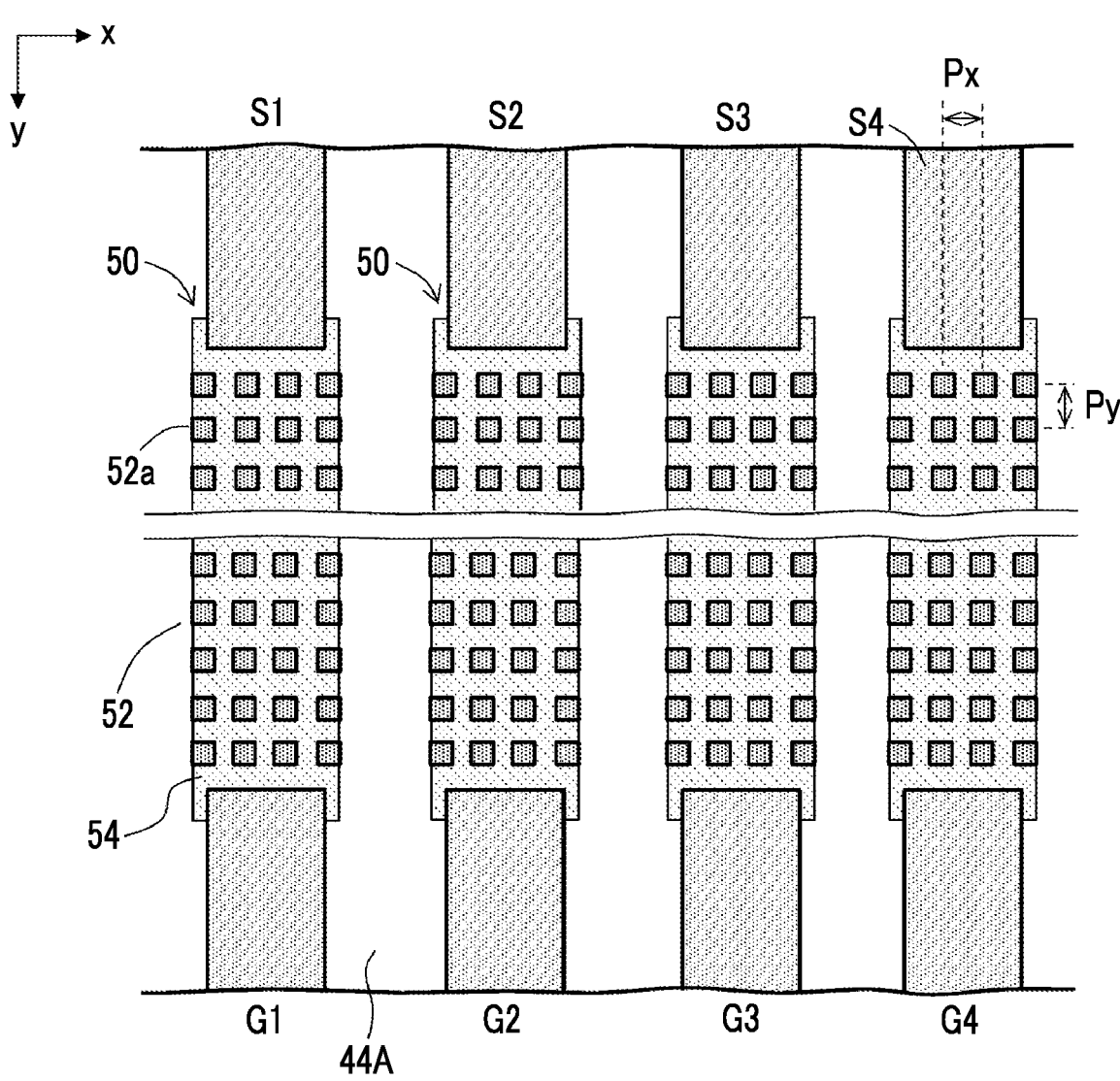
FIG. 5 is an xy cross-sectional view of the laminated structure according to the first example.

FIGS. 3 to 5 show a laminate according to a first example. The laminate is configured with a film member and a transducer array. In FIGS. 3 to 5, the laminate is in a spread state. In an assembling step of the probe, the laminate is rounded. In each of FIGS. 3 to 5, an x direction is a direction of a transducer arrangement direction, and a y direction is a direction orthogonal to the transducer arrangement direction and is a direction parallel to a central axis of the probe. The z direction is a lamination direction and an ultrasound wave propagation direction. In a case where the laminate is rounded, the z direction coincides with a radial direction.

FIG. 3 shows an xz cross section of the laminate according to the first example. In FIG. 3, a lower side is a living body side, and an upper side is a side close to the central axis of the probe.

As described above, the film member 34 is configured with the FPC substrate, and specifically, is configured with a base film 44 and a conductor layer 46 formed on the base film 44. The base film 44 is configured with a resin having insulating properties, and is configured with, for example, polyimide. The conductor layer 46 has wiring patterns and a plurality of acoustic element arrays 52. The wiring pattern includes a signal pattern and a ground pattern. The conductor layer 46 is configured with, for example, copper. The conductor layer 46 may be configured with gold, silver, nickel, or the like. In any case, the conductor layer 46 is configured with a conductive material that can be used as a wiring pattern material.

The transducer array 18 is fixed to a surface of the film member 34 on a non-living body side. The transducer array 18 is configured with the plurality of transducers 18a arranged in the x direction. Each of the transducers 18a is configured with a piezoelectric material. The transducer 18a has a signal electrode layer and a ground electrode layer. However, the signal electrode layer and the ground electrode layer are not shown in FIG. 3.

A plurality of acoustic matching layers 50 are provided between the base film 44 and the plurality of transducers 18a. In other words, the plurality of acoustic matching layers 50 are provided within a thickness range in which the conductor layer 46 is present. Each acoustic matching layer 50 consists of an acoustic element array 52 and a filling material 54. The acoustic element array 52 has a gap. The gap is filled with the filling material 54.

As shown in FIG. 5, each acoustic element array 52 is configured with a plurality of acoustic elements aligned in the x direction and the y direction. As described above, each acoustic element is configured with, for example, copper. A shape of each acoustic element is a cube or a rectangular parallelepiped. The filling material 54 is configured with an adhesive material, and is configured with, for example, an epoxy resin.

As described later, the plurality of transducers 18a are formed by dicing the piezoelectric material after a plate-shaped piezoelectric material is adhered to the film member 34 in the spread state. Slits 56 are generated between two adjacent transducers 18a by dicing. After the laminate is rounded, a packing material may fill each slit 56. A reference numeral 58 indicates a groove formed on a surface of the base film by dicing.

The base film 44 and each transducer 18a are adhered to each other through the acoustic matching layer 50. As described above, each acoustic matching layer 50 is configured with the acoustic element array 52 and the filling material 54 that fills a gap included in the acoustic element array 52. A reference numeral 57 denotes ultrasound waves transmitted from each transducer 18a. Ultrasound waves 57 transmit through blood and a vascular wall.

In each transducer 18a, a thickness t1 is, for example, 60 µm to 80 µm, and a width w1 in the x direction is, for example, 30 µm to 50 µm. A width of each transducer 18a in the y direction (w3 described later) is, for example, 0.6 mm to 0.8 mm. A pitch between the transducers is, for example, 60 µm to 80 µm. A width w2 of the slit 56 is, for example, 10 m to 20 µm. A thickness of each acoustic matching layer is the same as a thickness t2 of the conductor layer, and the thickness t2 is, for example, 4 µm to 100 m and is desirably 15 µm to m. A thickness t3 of the base film 44 is 10 µm to 30 µm. The width of each of alignment elements in the x direction and the width of each of the alignment elements in the y direction are, for example, 2 µm to 15 m, respectively. All numerical values shown in the present specification are merely examples.

In a case where a wavelength corresponding to the center frequency of the ultrasound waves is expressed as $\lambda$, the thickness t2 of each acoustic matching layer 50 satisfies a condition of $\lambda/10 \leq t2 < \lambda/2$. By satisfying the above-described condition, each of the acoustic matching layers 50 exhibits a satisfactory acoustic matching action. A lower limit in the condition may be $\lambda/8$. It is desirable that $t2 = \lambda/4$. The center frequency of the ultrasound waves is generally a frequency corresponding to a center between two points at which a frequency is lowered by $-6$ dB from a peak in frequency characteristic included in the transducer array.

An acoustic impedance Z1 of each transducer 18a is, for example, 30 MRayl, an acoustic impedance Z2 of each acoustic matching layer 50 is, for example, 8 MRayl to 10 MRayl, and an acoustic impedance Z3 of the base film 44 is, for example, 3 MRayl. An acoustic impedance Z4 of the living body is generally 1.5 MRayl. Z2 is smaller than Z1 and is larger than Z4. In the embodiment, a relationship of Z1>Z2>Z3>Z4 is established.

FIG. 4 shows a yz cross section of the laminate according to the first example. On the base film 44 included in the film member 34, a signal pattern S and a ground pattern G are formed, and an acoustic element array 52 is formed between the signal pattern S and the ground pattern G.

The transducer 18a is configured with a piezoelectric material 48. An electrode layer 60 is formed on two surfaces of the piezoelectric material 48 orthogonal to the y direction and on two surfaces of the piezoelectric material 48 orthogonal to the z direction. The electrode layer 60 is formed by a method such as gold vapor deposition.

Two separation grooves 62 and 64 are formed in the piezoelectric material 48. The electrode layer 60 is divided into a signal electrode layer 60a and a ground electrode layer 60b by the two separation grooves 62 and 64. The signal electrode layer 60a is connected to the signal pattern S, and the ground electrode layer 60b is connected to the ground pattern G.

The transducer 18a has a living body side end portion. The living body side end portion includes a first portion 200 and a second portion 202 that are separated in the y direction. The first portion 200 is mounted on the signal pattern S, and the second portion 202 is mounted on the ground pattern G. The acoustic element array 52 is provided between the signal pattern S and the ground pattern G (refer to reference numeral 204).

The acoustic matching layer 50 is formed between the base film 44 and the transducer 18a. The acoustic matching layer 50 consists of the acoustic element array 52 and the filling material 54. The acoustic element array 52 is configured with a plurality of acoustic elements two-dimensionally arranged. The plurality of acoustic elements are connected to the ground electrode layer 60b. As a result, the acoustic element array 52 is prevented from static charging. The acoustic matching layer 50 is formed within a thickness range included in the conductor layer. As a result, an increase in a thickness of the laminate is avoided. In addition, FIG. 4 shows a width w3 of the transducer 18a in the y direction.

FIG. 5 shows an xy cross section of the laminate according to the first example. As described above, the transducer array is configured with several tens or several hundreds of transducers, and the acoustic matching layer 50 is provided for each of the transducers. FIG. 5 shows four acoustic matching layers 50. In addition, in FIG. 5, four signal lines S1 to S4 in the signal pattern and four ground lines G1 to G4 in the ground pattern are shown.

Each acoustic matching layer 50 is configured with the acoustic element array 52 and the filling material 54. Each acoustic element array 52 is configured with the plurality of acoustic elements two-dimensionally arranged. Each acoustic element array 52 is uniformly embedded in the acoustic matching layer 50. The acoustic element array 52 has a lattice-shaped gap, and the gap is filled with the filling material 54. A width of each of the signal lines S1 to S4 in the x direction and a width of each of the ground lines G1 to G4 in the x direction are, for example, 30 µm. A pitch of the signal lines S1 to S4 in the x direction and a pitch of the ground lines G1 to G4 in the x direction are, for example, 30 µm.

By manipulating a ratio of the filling material and a ratio of the conductive material in each of the matching layers 50, a desired acoustic impedance can be obtained. Here, the ratio is a volume ratio. For example, in a case where an acoustic impedance of the filling material is expressed as Za, an acoustic impedance of copper is expressed as Zb, and an acoustic impedance targeted in the matching layer is expressed as Zx, an area ratio $\alpha$ of the filling material and an area ratio $\beta$ of the conductive material may be determined such that following calculation expressions are established.

$$Zx = \alpha Za + \beta Zb \tag{1}$$

Here, each of the area ratio $\alpha$ and the area ratio $\beta$ is an area ratio in the xy cross section, and $\alpha + \beta = 1$.

For example, in a case where Za is 3 MRayl, Zb is 40 MRayl, and Zx is 10 MRayl, $\alpha$ is set to 0.81 and $\beta$ is set to 0.19. Therefore, in a case where the ratio of the filling material is set to 80% and the ratio of the conductive material is set to 20%, a target acoustic impedance of 10 MRayl of the acoustic matching layer can be obtained.

As shown in FIG. 5, each acoustic element array 52 has a pitch Px in the x direction and a pitch py in the y direction. In a case where a wavelength of the transverse wave that may be generated due to the filling material and pitches Px and Py match, stationary waves are generated. The above-described unnecessary vibration deteriorates characteristics of the array transducer. In a case where a frequency of the ultrasound wave is expressed by f, a wavelength of the transverse wave is expressed by $\lambda t$, and a velocity of the transverse wave is expressed by ct, a condition is as follows, under which the stationary waves are generated.

$$\lambda t = ct / f \tag{2}$$

The frequency of the ultrasound wave is, for example, a center frequency in frequency characteristics included in the transducer array. In a case where Px and Py are smaller than $\lambda t$, the stationary waves are not generated. For example, in a case where f is 20 MHz and ct is 1360 m/s, both Px and Py may be 68 μm or less.

Figure 6:
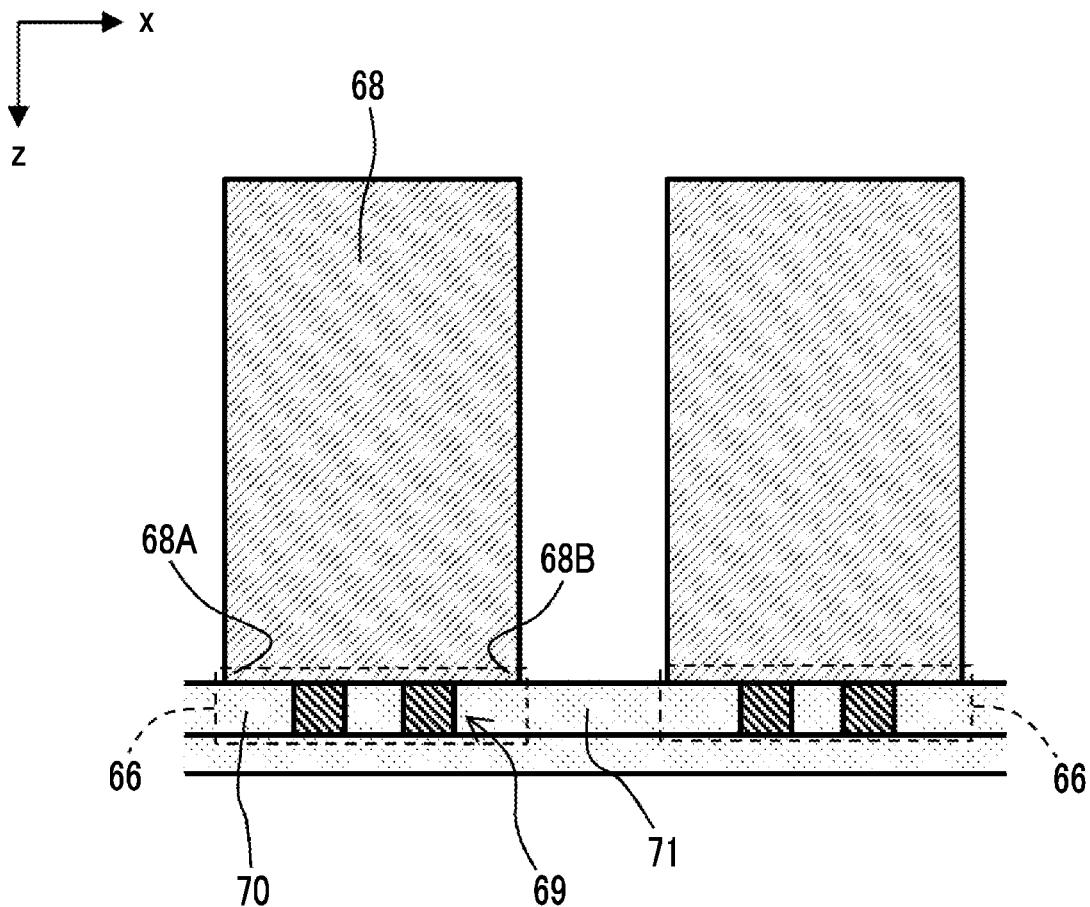
FIG. 6 is a view showing a support action of a matching element array having a first array pattern.
Figure 7:
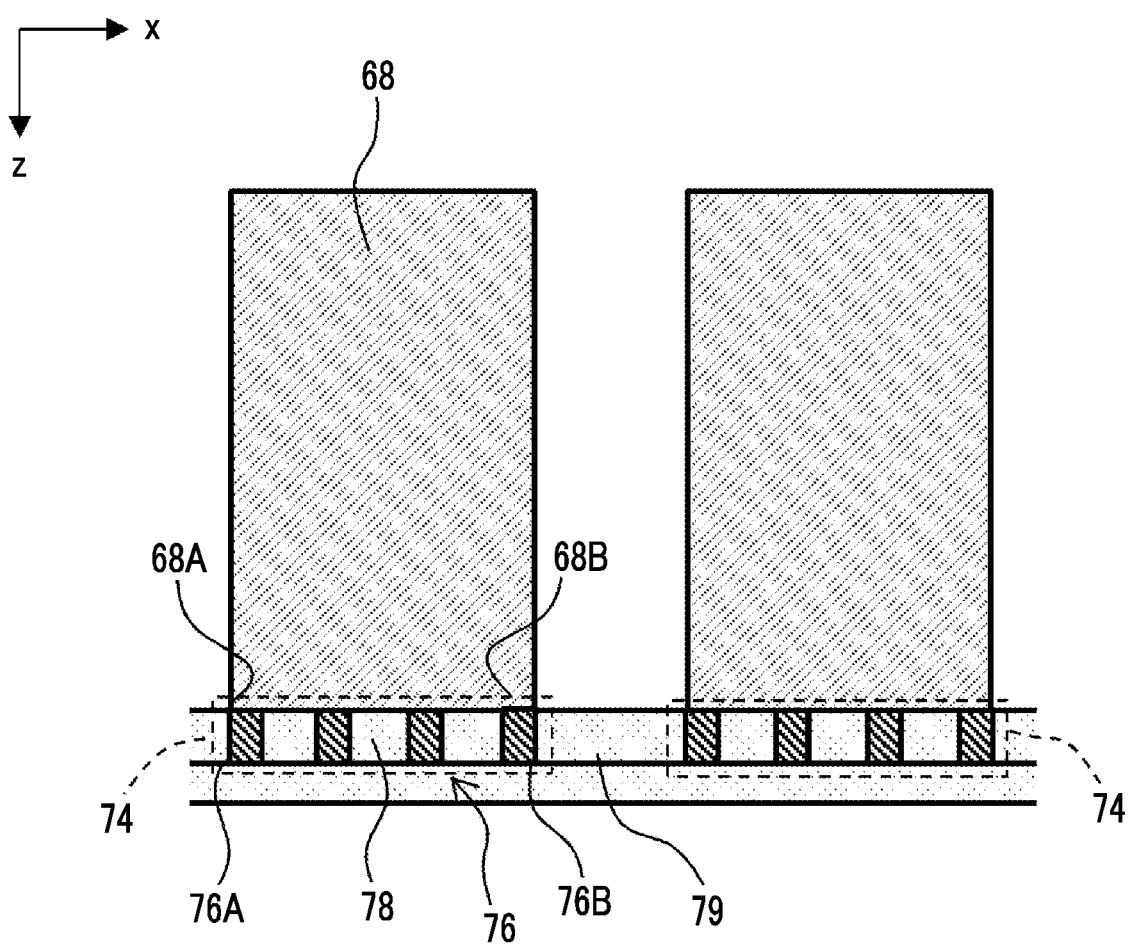
FIG. 7 is a view showing a support action of a matching element array having a second array pattern.

FIG. 6 shows an acoustic element array 69 having a first array pattern, and FIG. 7 shows an acoustic element array 76 having a second array pattern. An xy cross-sectional area of the acoustic element array 69 and an xy cross-sectional area of the acoustic element array 76 are the same.

In FIG. 6, each acoustic matching layer 66 includes the acoustic element array 69 and a filling material 70. The living body side end portion of each transducer 68 includes a first corner portion 68A and a second corner portion 68B extending in the y direction. The first corner portion 68A and the second corner portion 68B are separated in the x direction. An acoustic element is not present between the first corner portion 68A and the base film, and the first corner portion 68A is supported by the filling material 70. Similarly, the acoustic element is not present between the second corner portion 68B and the base film, and the second corner portion 68B is supported by the filling material 70. In an example shown in FIG. 6, a filling material 71 is provided between two adjacent acoustic matching layers. In a case where the acoustic element array 69 shown in FIG. 6 is used, since the first corner portion 68A and the second corner portion 68B are supported by relatively soft members, an abnormal vibration mode is likely to occur in the transducer 68.

In FIG. 7, each acoustic matching layer 74 includes the acoustic element array 76 and a filling material 78. In each transducer 68, an acoustic element 76A is present between the first corner portion 68A and the base film, and the first corner portion 68A is supported by the acoustic element 76A. Similarly, an acoustic element 76B is present between the second corner portion 68B and the base film, and the second corner portion 68B is supported by the acoustic element 76B. In an example shown in FIG. 7, a filling material 79 is provided between two adjacent acoustic matching layers. In a case where the acoustic element array 76 shown in FIG. 7 is used, since the entire living body side end portion of the transducer 68 is supported by a hard member, particularly, the first corner portion 68A and the second corner portion 68B are supported by a relatively hard member, the abnormal vibration mode is less likely to occur in the transducer 68.

Therefore, in a case where a pattern of a matching element array is designed, an amount of the conductive material included in a peripheral portion of the acoustic matching layer may be equal to or more than an amount of the conductive material included in a central portion of the acoustic matching layer. Particularly, the first corner portion and the second corner portion may be directly supported by the matching element array. Each of the peripheral portion and the central portion corresponds to 50% of the acoustic matching layer.

Figure 8:
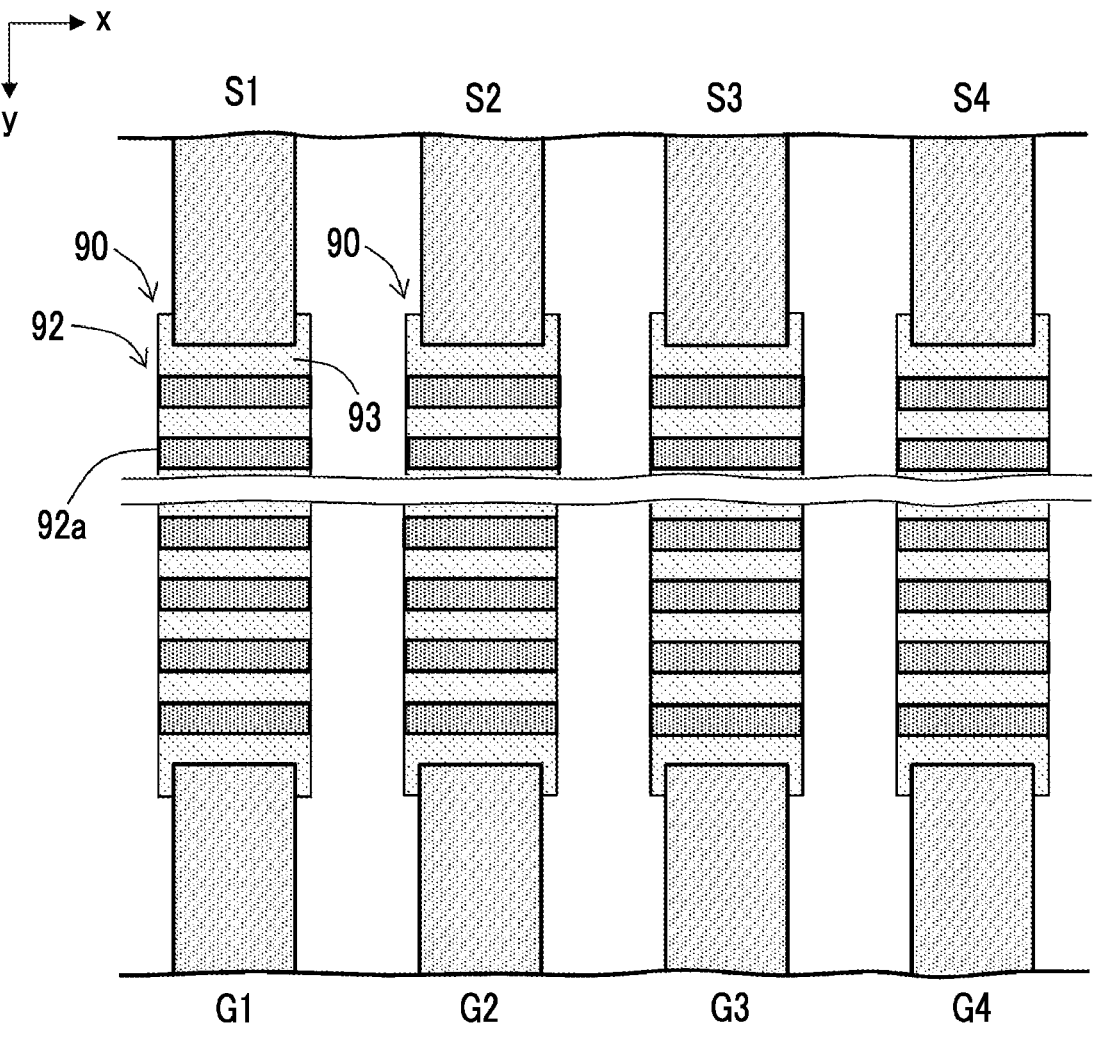
FIG. 8 is an xy cross-sectional view of a laminated structure according to a second example.

FIG. 8 shows an xy cross section of a laminate according to a second example. Each acoustic matching layer 90 is configured with an acoustic element array 92 and a filling material 93. The acoustic element array 92 is configured with a plurality of acoustic elements 92a aligned in the y direction. Each of the acoustic elements 92a has a plate shape extending in the x direction. In addition, FIG. 8 also shows a plurality of signal lines S1 to S4 and a plurality of ground lines G1 to G4.

Figure 9:
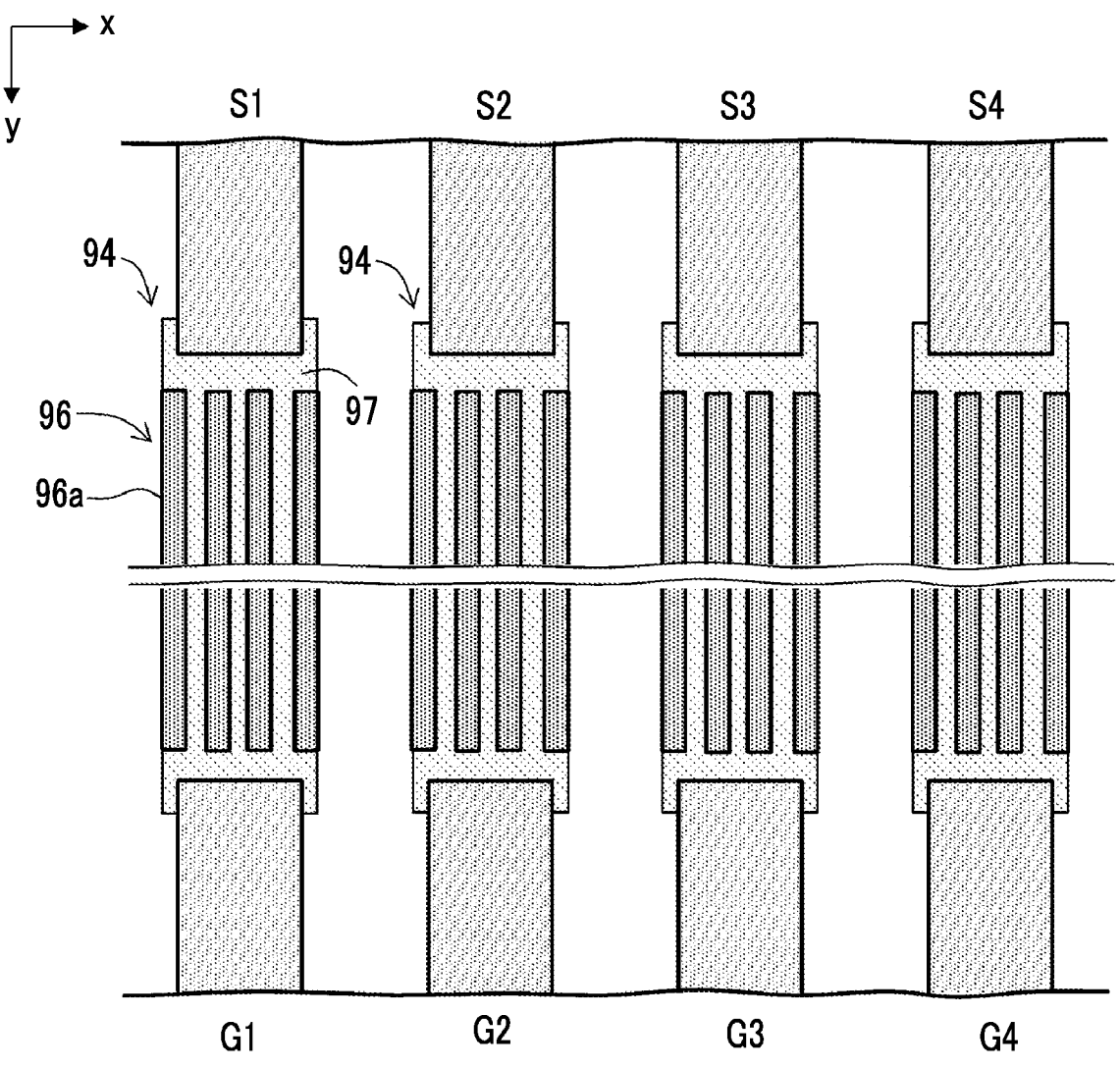
FIG. 9 is an xy cross-sectional view of a laminated structure according to a third example.

FIG. 9 shows an xy cross section of a laminate according to a third example. Each acoustic matching layer 94 is configured with an acoustic element array 96 and a filling material 97. The acoustic element array 96 is configured with a plurality of acoustic elements 96a aligned in the x direction. Each of the acoustic elements 96a has a plate shape extending in the y direction. In addition, FIG. 9 also shows the plurality of signal lines S1 to S4 and the plurality of ground lines G1 to G4.

Figure 10:
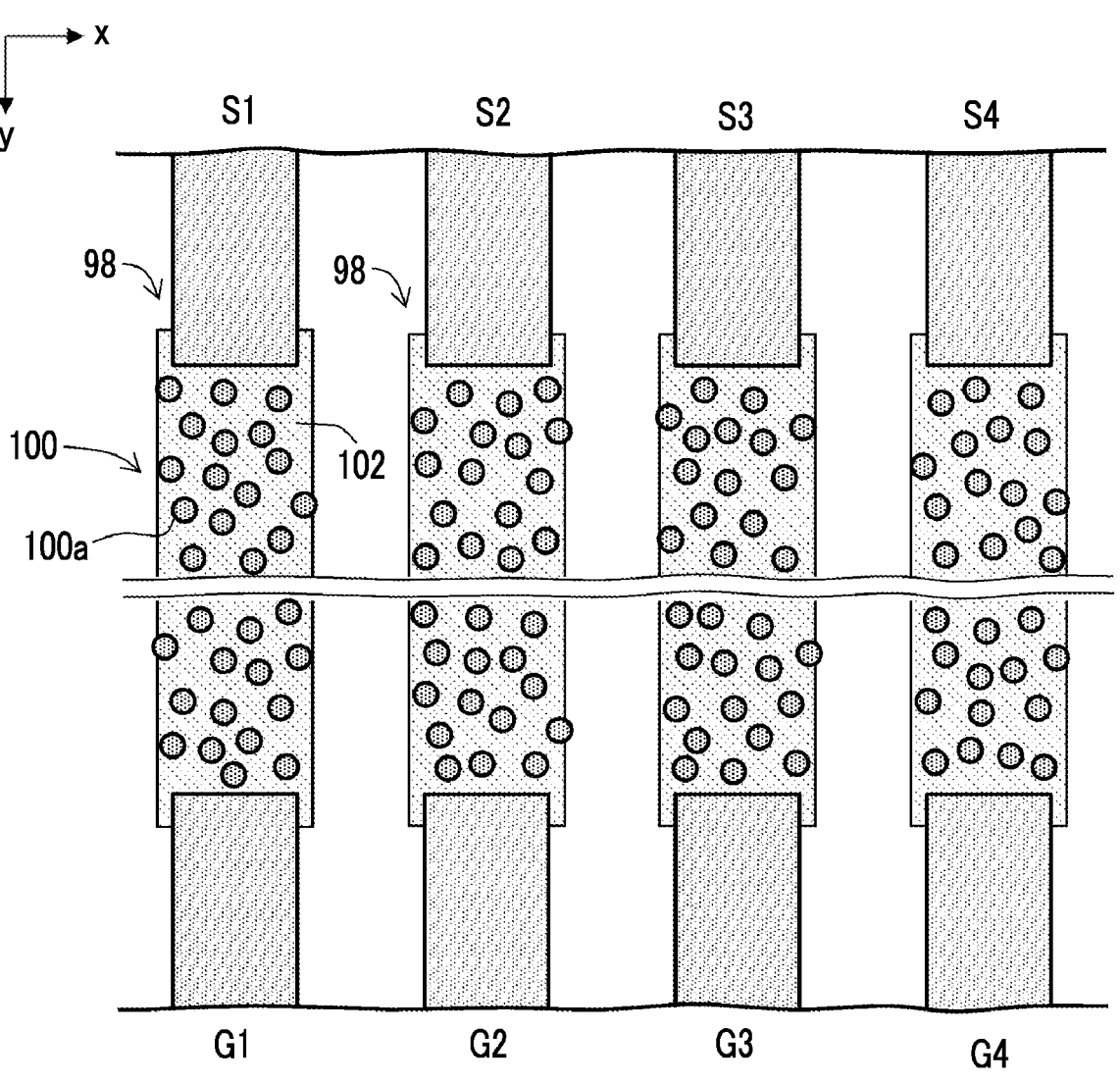
FIG. 10 is an xy cross-sectional view of a laminated structure according to a fourth example.

FIG. 10 shows the xy cross section of the laminate according to the third example. Each acoustic matching layer 98 is configured with an acoustic element array 100 and a filling material 102. The acoustic element array 100 is configured with a plurality of acoustic elements 100a two-dimensionally randomly disposed. Each acoustic element 100a has a cylindrical shape.

In addition, FIG. 10 shows the plurality of signal lines S1 to S4 and the plurality of ground lines G1 to G4.

In the laminate according to the second example, the third example, and a fourth example, each transducer has a structure shown in FIGS. 3 and 4. Each acoustic element array is connected to the ground pattern.

Figure 11:
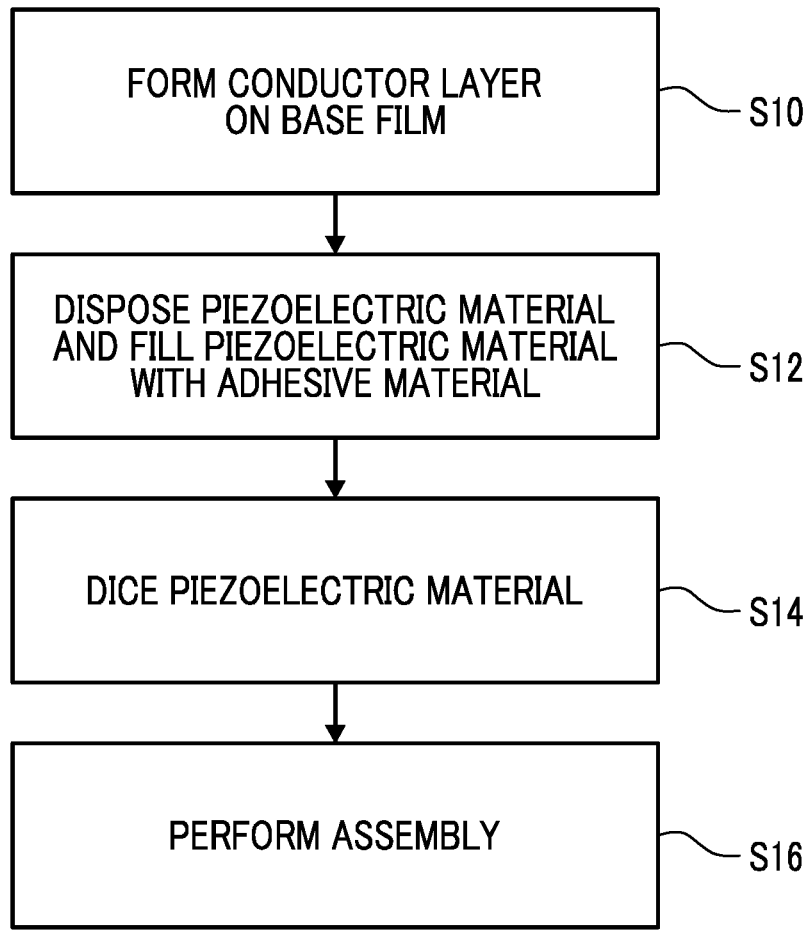
FIG. 11 is a flowchart showing a manufacturing method according to the embodiment.

FIG. 11 shows a method of manufacturing a probe according to the embodiment. The method of manufacturing a probe includes a method of manufacturing an acoustic matching layer.

In S10, the conductor layer is formed on the base film in the spread state, so that the film member is produced. In a case of forming the conductor layer, for example, a printing technique or a drawing technique is used. The conductor layer has wiring patterns and a plurality of acoustic element arrays. The wiring pattern includes a signal pattern and a ground pattern.

In S12, a plate-shaped piezoelectric material is provided on the film member. In this case, the filling material is introduced between the base film and the piezoelectric material. As a result, the piezoelectric material is fixed to the film member. At the same time, the plurality of acoustic matching layers are completed. In S14, the piezoelectric material is diced, so that a plurality of transducers are produced.

In S16, the laminate consisting of the film member and the transducer array is rounded in a circular shape, and the laminate is adhered to a backing. Another member is attached to an assembly produced in S16.

According to the above-described embodiment, it is possible to provide the acoustic matching layer for each transducer while the thickness of the laminate is suppressed. By adjusting the pattern of the acoustic element array in the acoustic matching layer, a desired acoustic impedance can be easily obtained. An additive may be mixed in the filling material. A second acoustic matching layer may be provided separately from the first acoustic matching layer including the acoustic element array.

The present application claims priority from Japanese Patent Application No. 2023-066850 filed on Apr. 17, 2023, the content of which is hereby incorporated by reference into this application.

What is claimed is:

1. A body cavity insertion-type ultrasound probe comprising:
    a film member including a base film and a conductor layer formed on the base film, the conductor layer being configured with electrically conductive material; and
    a plurality of transducers provided on the film member, wherein
    a plurality of acoustic matching layers are provided between the base film and the plurality of transducers,
    the conductor layer includes a wiring pattern electrically connected to the plurality of transducers and a plurality of acoustic element arrays embedded in the plurality of acoustic matching layers, each of the plurality of acoustic element arrays being configured with a plurality of acoustic elements,
    each of the acoustic matching layers is configured with a respective one of the plurality of acoustic element arrays and a gap included in the respective one of the plurality of acoustic element arrays, and
    the gap in each of the acoustic matching layers is filled with a filling material.

2. The body cavity insertion-type ultrasound probe according to claim 1, wherein an acoustic impedance of each of the acoustic matching layers is smaller than an acoustic impedance of each of the transducers and is larger than an acoustic impedance of a living body tissue.

3. The body cavity insertion-type ultrasound probe according to claim 1, wherein an acoustic impedance of each of the acoustic matching layers is an acoustic impedance in accordance with a presence ratio of a conductor material in each of the acoustic matching layers.

4. The body cavity insertion-type ultrasound probe according to claim 1, wherein
    the wiring pattern includes a signal pattern and a ground pattern, a living body side end portion of each of the transducers includes a first portion and a second portion separated in a direction orthogonal to a transducer arrangement direction,
    the first portion in each of the transducers is connected to the signal pattern,
    the second portion in each of the transducers is connected to the ground pattern, and
    for each acoustic element array amongst the plurality of acoustic element arrays, the acoustic element array is provided between the living body side end portion and the base film and between the signal pattern and the ground pattern, in each of the transducers.

5. The body cavity insertion-type ultrasound probe according to claim 4, wherein a thickness of the signal pattern, a thickness of the ground pattern, and a thickness of each of the acoustic element arrays are the same.

6. The body cavity insertion-type ultrasound probe according to claim 1, wherein the plurality of acoustic element arrays are electrically connected to a ground pattern included in the wiring pattern.

7. The body cavity insertion-type ultrasound probe according to claim 1, wherein
    a thickness of each of the acoustic element arrays is the same as a thickness t of each of the acoustic matching layers, and
    the thickness t satisfies a condition of $\lambda/10 \leq t < \lambda/2$, in a case where a wavelength corresponding to a center frequency of ultrasound waves emitted from each of the transducers is expressed by $\lambda$.

8. The body cavity insertion-type ultrasound probe according to claim 1, wherein
    each of the transducers includes a living body side end portion including two corner portions that extend in a direction orthogonal to a transducer arrangement direction, and
    each of the acoustic element arrays includes a plurality of acoustic elements supporting the two corner portions.

9. The body cavity insertion-type ultrasound probe according to claim 1, wherein for each acoustic element array amongst the plurality of acoustic element arrays, a pitch included in the acoustic element array in each of the acoustic matching layers is smaller than a wavelength of a transverse wave generated by the filling material.

10. The body cavity insertion-type ultrasound probe according to claim 1, wherein
    the film member has a circular-shaped form,
    the plurality of transducers are circularly aligned inside the film member, and
    ultrasound waves emitted from each of the transducers pass through the film member.

11. The body cavity insertion-type ultrasound probe according to claim 1, wherein the gap filled with the filling material is lattice-shaped.

* * * * *